US00PP07814P

United States Patent [19]

McKenzie, deceased et al.

[11] Patent Number: Plant 7,814

[45] Date of Patent: Mar. 3, 1992

[54] APPLE TREE NAMED 'SCIROS'

[76] Inventors: Don McKenzie, deceased, late of Havelock North; by Joy McKenzie, personal representative, P.O. Box 8345, Havelock North; Allan G. White, R.D. 2, Hastings, all of New Zealand

[21] Appl. No.: 566,285

[22] Filed: Aug. 13, 1990

[51] Int. Cl.[5] ..... A01H 5/00
[52] U.S. Cl. ..... Plt./34
[58] Field of Search ..... Plt./34

[56] References Cited

U.S. PATENT DOCUMENTS

P.P. 2,460 12/1964 Roberts ..... Plt. 34
P.P. 3,637 10/1974 McKenzie ..... Plt. 34

*Primary Examiner*—James R. Feyrer
*Attorney, Agent, or Firm*—Quarles & Brady

[57] ABSTRACT

The new and distinct variety is a selection from seedlings derived from crossing the apple varieties known as "Gala" (U.S. Plant Pat. No. 3,637) and "Splendour" (U.S. Plant Pat. No. 2,460). The fruit of the apple tree of this new variety has an attractive appearance characterized by its overall bright red color pattern. The new variety has been named "Sciros".

1 Drawing Sheet

SUMMARY OF THE INVENTION

The new variety was selected from a population seedlings derived from crossing the apple varieties "Splendour" (U.S. Plant Pat. No. 2,460) and "Gala" (U.S. Plant Pat. No. 3,637) in 1984. The new variety was distinguishable from the parent varieties Splendour and Gala as well as the varieties Sciray; Sciglo; and Scieur (subject of co-pending applications filed on even date herewith by the same applicants). The features which distinguish the new variety from the aforementioned varieties are:

Gala: Later season, larger fruit size, block colour pattern, rose pink colour, more rounded shape.
Splendour: Taller fruit shape, less russet, later harvest season, firmer flesh, thicker skin.
Sciray: Later season, rounder shape, block colour pattern, rose-pink colour.
Sciglo: Later season, larger fruit size, rose-pink colour, block colour pattern, higher aroma.
Scieur: Later season, larger fruit size, fruit shape taller, rose-pink colour, fruit colour pattern block.

The new variety has been named the "Sciros" variety. Asexual propagation by budding shows that the unique combination of characteristics and distinctive colour come true to form and are established and transmitted through succeeding propagations.

BRIEF DESCRIPTION OF THE DRAWINGS

The accompanying drawings show typical specimens of the foliage and fruit of the new variety as depicted in colours as nearly true as is reasonably possible to make the same in a colour illustration of this character.

View A is a side view of an apple of the variety.

View B is a bottom view of an apple of the variety.

View C is a cross sectional view of an apple of the variety.

View D is a top view of an apple of the variety.

Figure 1:
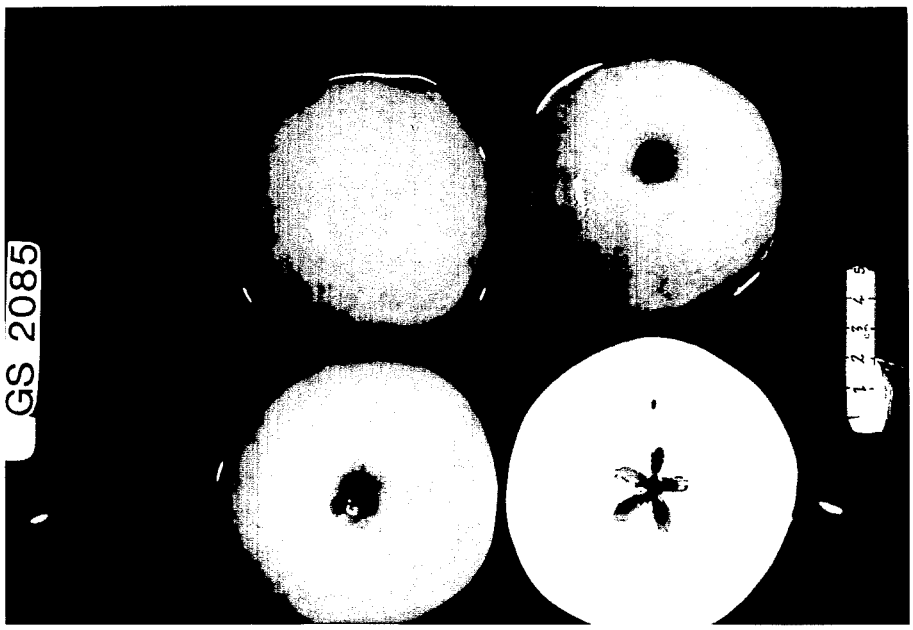
FIG. 1 represents four views of an apple of the new variety.
Figure 2:
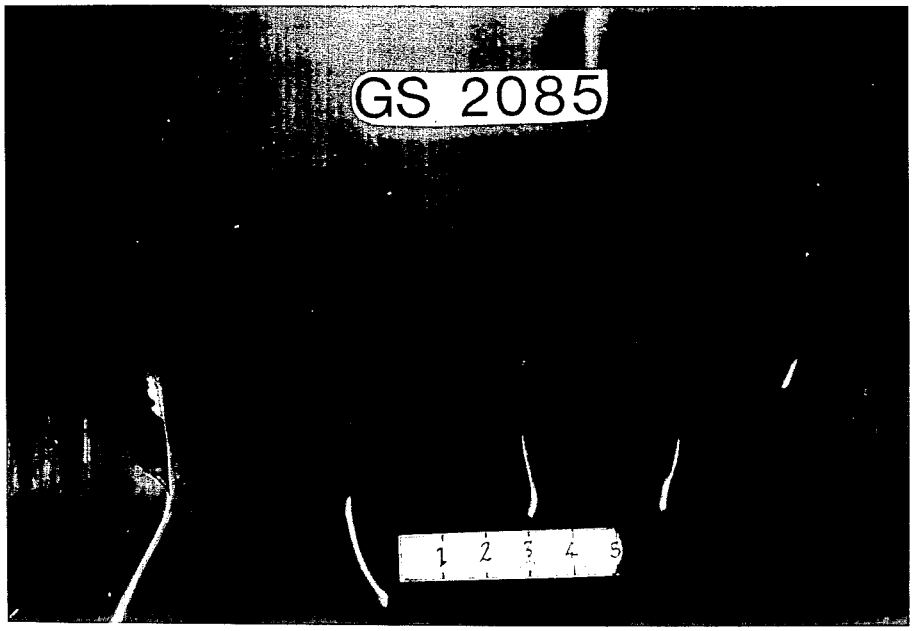

FIG. 2 is a view showing five leaves of the variety.

DETAILED DESCRIPTION OF THE DISCLOSURE

The following is a detailed description of the new variety with color terminology in accordance with The Royal Horticultural Society Colour Chart (RHSCC) except where general color terms of ordinary meaning are used as is clear from the context.

The specimens described were grown at Havelock North, New Zealand. The observations were made in the 1989 season on trees which were three years old at the time.

The fruit ripened for eating towards late season. Specifically harvest commences about April 8 and ends about May 10 in New Zealand. The trees flowered in early October. Specifically blossom commences about October 2 and full bloom occurs about October 20 in New Zealand.

Tree: Medium-small; upright habit; bearing, on spurs; vigor medium with annual growth for five year old trees with MM106 rootstock being about 275 mm; spurs occurring at a rate of 3.5 per 10 cm. on three year old growth.

Trunk: Moderately rough; size, medium; the bark is RHSCC 200C when new and RHSCC 199A when old.

Branches: Thin; moderately rough; moderate branching; the angle of branching being commonly 25 degrees above the horizontal; the spread-to-height ratio being about 1.5 to 2.5.

Lenticels: Average; large.

Leaves:

*Length.*—4 15/16 inches.

*Width.*—2⅜ inches; medium size; outward pose; medium length/width ratio of blade; upfolded to concave shape in cross section; serrate indentation of margin; medium glossiness of upper side; medium pubescence on lower side; medium petiole length; medium stipule size, medium time of bud burst; the color of the blade is RHSCC 137C, the stems are RHSCC 157A and 180C, and the veins are RHSCC 157A.

Flowers: Medium time of beginning of flowering (10% flowers); medium size; flat shape; margin of petals, overlapping; colour of bud just before flower opens, pink.

Fruit: Examined at peak maturity.

*Soluble solids.*—13.73.

*Size.*—Large; axial diameter, 2 9/16 inches; transverse diameter 2 5/6 inches.

*Shape.*—Uniform; long cylindrical to ellipsoid; symmetrical in side view; ribbing present; medium crowning at distal end.

*Cavity.*—Medium depth; medium width.

*Basin.*—Medium to deep depth; medium to broad width; ribbing present.

*Stem.*—Medium thickness (comparable to Cox's Orange Pippin); medium length (comparable to Granny Smith).

*Calyx.*—Open 10% of fruit; calyx tube length, long; calyx tube width, wide; calyx tube shape, U or V shape.

*Sepal.*—Length, medium; spacing, free.

*Eye.*—Size, large; aperture, open.

*Skin.*—Medium; smooth; bloom of skin, present; greasiness of skin, absent; cracking tendency of skin, absent; background colour, yellow-green RHSCC 2C.

*Over colour.*—Approximately fifty percent of over colour of skin; rosepink blush (red) RHSCC 46C; solid flush; weak amount of russet around stalk cavity.

*Flesh.*—Juicy; firm; yellowish; crisp; Penetrometer equals 7.12 kg.; medium browning of flesh (1 hour after cutting, stainless steel blade).

*Texture.*—Fine.

*Flavour.*—Strong sweetness, medium acidity (pH about 4.36); sweet with acid balance; similar acid than Gala, more aromatic than Splendour.

*Weight of fruit.*—250 gm.

*Quality.*—Excellent.

*Core.*—Distinctness of core line in cross section (median through locules), weak; aperture of locules in cross section, open; central cavity (in cross section), absent.

*Sinus.*—Closed.

*Seeds.*—Five locules; 8 to 10 seeds total, 2 seeds per locule maximum; seed length 7 mm.; seed width 4 mm.; form obtuse; color RHSCC 166C.

Use: Market; dessert.

Keeping quality: Very good; no disorders after 98 days.

Resistance to:

*Insects.*—Good.

*Dieases.*—Good.

Production: Early and regular cropping; tendency to biennial bearing if overcropped.

Growth habit: Standard, fruit bourne on short spurs.

Management: Trees require pruning in winter and fruit thinning in early summer. Trees in test plot trained as center leader trees. Natural habit is an open textured narrow conic tree with low to moderate branching.

It is claimed:

1. A new and distinct variety of apple tree which is selected from seedlings derived from crossing the apple varieties known as Splendour (U.S. Plant Pat. No. 2,460) and Gala (U.S. Plant Pat. No. 3,637) substantially as shown and described, characterised by its overall bright red colour and sweet flavour.

* * * * *